(12) United States Patent
Hollander

(10) Patent No.: US 8,461,148 B2
(45) Date of Patent: Jun. 11, 2013

(54) USE OF MEMANTINE (NAMENDA) TO TREAT AUTISM, COMPULSIVITY AND IMPULSIVITY

(75) Inventor: Eric Hollander, Mamaroneck, NY (US)

(73) Assignee: Icahn School of Medicine at Mount Sinai, New York, NY (US)

(*) Notice: Subject to any disclaimer, the term of this patent is extended or adjusted under 35 U.S.C. 154(b) by 0 days.

(21) Appl. No.: 11/575,483

(22) PCT Filed: Sep. 19, 2005

(86) PCT No.: PCT/US2005/033467
§ 371 (c)(1),
(2), (4) Date: Jan. 16, 2008

(87) PCT Pub. No.: WO2006/034187
PCT Pub. Date: Mar. 30, 2006

(65) Prior Publication Data
US 2008/0249082 A1    Oct. 9, 2008

Related U.S. Application Data

(60) Provisional application No. 60/611,534, filed on Sep. 20, 2004.

(51) Int. Cl.
*A61K 31/13* (2006.01)

(52) U.S. Cl.
USPC .......................................................... 514/220

(58) Field of Classification Search
USPC .......................................................... 514/220
See application file for complete search history.

(56) References Cited

U.S. PATENT DOCUMENTS

| 6,387,956 B1 * | 5/2002 | Shapira et al. ............... 514/646 |
| 7,456,224 B2 * | 11/2008 | Chez ........................... 514/662 |
| 2005/0282911 A1 * | 12/2005 | Hakkarainen et al. ........ 514/662 |

OTHER PUBLICATIONS

Chez et al (Memantine experience in children and adolescents with autistic spectrum disorders. Annals of Neurology. (published online Aug. 31, 2004); 56(8):p. S109.*

* cited by examiner

*Primary Examiner* — Jake M. Vu
(74) *Attorney, Agent, or Firm* — Marshall, Gerstein & Borun LLP

(57) ABSTRACT

The present invention relates to the treatment of compulsive, impulsive and pervasive developmental disorders. More particularly, the methods described herein comprise administration of memantine to an individual suffering from such a disorder in an amount effective to relieve one or more symptoms of said disorder. In particularly preferred aspects, the invention is directed to the use of memantine for the treatment of autism.

21 Claims, No Drawings

USE OF MEMANTINE (NAMENDA) TO TREAT AUTISM, COMPULSIVITY AND IMPULSIVITY

FIELD OF THE INVENTION

The present invention relates to the use of memantine to treat a variety of compulsive, impulsive, and pervasive developmental disorders.

BACKGROUND OF THE INVENTION

"Obsessive-compulsive spectrum disorders" is an overarching category of disorders that includes a variety of compulsive, impulsive, and pervasive developmental disorders. These disorders share features with obsessive-compulsive disorder, including symptoms such as repetitive thoughts and behaviors. Obsessive-compulsive disorder (OCD) is one disorder that may be included within this category. Other disorders that are included within this category are listed herein, and include somatoform disorders, eating disorders, impulse control disorders, movement disorders including Tourette's syndrome and Sydenham's chorea, and pervasive developmental disorders, including autism, Asperger's syndrome and Pervasive Developmental Disorder not otherwise specified (PDD-NOS).

Obsessive-compulsive disorder (OCD) is now recognized as a common disorder that has a life-time prevalence in the United States ranging from 1.9% to 3.3% (Shapira et al., Depression and Anxiety 6; 170-173 (1997).) There are a number of well-recognized diagnostic criteria for OCD (Diagnostic and Statistical Manual of Mental Disorders, fourth edition; DSM-IV). Such criteria include obsessions or compulsions, which the individual has, at some point during the course of the disorder recognized, that the obsessions or compulsions are excessive or unreasonable; the obsessions or compulsions caused marked stress, are time-consuming or significantly interfere with the person's normal routine, occupational/academic functioning, or usual social activities or relationships; if another axis I disorder is present, the content of the obsessions or compulsions is not restricted to it; and the disturbance is not due to the direct physiologic effects of a substance or a general medical condition.

According to the DSM-IV, indicia of obsessions include the person having recurrent and/or persistent thoughts, impulses or images that are experienced at some time during the disturbance as intrusive and inappropriate and as causing marked anxiety or distress. Typically, the thoughts, impulses or images are not simply excessive worries about real-life problems. Third, the person attempts to ignore or suppress such thoughts, impulses or images or to neutralize them through some other thought or action. Fourth, the person recognizes that the obsessional thoughts, impulses, or images are products of his or her own mind and are not imposed from without.

The DSM-IV also sets forth diagnostic criteria as indicia of compulsion. In compulsive disorders, the person has repetitive behaviors or mental acts that the person feels driven to perform in response to an obsession or according to rules that must be applied rigidly. Repetitive behaviors include hand washing, ordering and checking, while mental acts include praying, counting and repeating words silently. Second, the behaviors or mental acts are aimed at preventing some dreaded event or situation; however, these behaviors or mental acts either are not connected in a realistic way to what they are designed to neutralize or prevent, or are clearly excessive.

Individuals who meet the DSM-IV criteria for OCD can be scored using the Yale-Brown Obsessive-Compulsive Scale (Y-BOCS). Y-BOCS scores range from 0 to 40. Generally, 0 to 7 is considered a subclinical syndrome, 8-15 is considered mild, 16-23 is considered moderate, 24-31 is considered severe, and 32-40 is considered extremely severe. This scale is further discussed in e.g., U.S. Pat. No. 6,387,956 (incorporated herein by reference in its entirety). Other U.S. patents that generally provide discussion of methods of evaluating and treating OC disorders include e.g., U.S. Pat. No. 6,420,351; U.S. Pat. No. 6,410,527; U.S. Pat. No. 6,632,429; U.S. Pat. No. 6,716,416; U.S. Pat. No. 6,667,297; and U.S. Pat. No. 6,512,010. Each of these patents is incorporated herein by reference in its entirety.

A wide range of psychiatric and neuropsychiatric disorders appear to be related to OCD and form a family of related disorders referred to as obsessive-compulsive (OC) spectrum disorders. OC spectrum disorders include somatoform disorders, eating disorders, impulse control disorders (ICDs), paraphilia and nonparaphilic sexual addictions, Sydeham's chorea, torticollis, autism, and movement disorders, including Tourette's syndrome.

Somatoform disorders include body dysmorphic disorder (BDD) and hyperchondriasis. Body dysmorphic disorder (BDD) is a preoccupation with an imagined slight defect in appearance that causes significant distress or impairment in functioning. Individuals suffering from BDD have preoccupations similar to OCD obsessions in that they have repetitive intrusive thoughts, often perform time-consuming, repetitive and sometimes ritualistic behaviors. Hypochondriasis is a preoccupation with the fear of having, or the idea that one has, a serious disease based on the person's misinterpretation of bodily signs or symptoms. Hypochondriacal preoccupations resemble OCD obsessions in that they are often experienced as intrusive and persistent, and the individuals often display repetitive checking behaviors.

Eating disorders include anorexia nervosa, bulimia nervosa and binge eating disorder (BED). The DSM-IV defines anorexia nervosa as a refusal to maintain a minimally normal body weight; intensive fear of gaining weight or becoming fat even though underweight; significant disturbance in perception of body shape or size; and, in females, amenorrhea. The DSM-IV defines bulimia nervosa as recurrent episodes of binge eating followed by inappropriate compensatory behaviors designed to prevent a weight gain. BED is characterized by recurrent episodes of binge eating in the absence of regular use of inappropriate compensatory behaviors. There is some overlap among anorexia nervosa, bulimia nervosa, and BED. However, all three disorders are characterized by a core preoccupation with food and body weight. Individuals suffering from eating disorders often perform specific rituals, and have an abnormal preoccupation with food and weight.

The DSM-IV defines an impulse control disorder (ICD) as the failure to resist the impulse, drive or temptation to perform some act that is harmful. ICDs include intermitted explosive disorder (IED), compulsive buying or shopping, repetitive self-mutilation (RSM), onychophagia, psychogenic excoriation, kleptomania, pathological gambling, and trichotillomania. Most individuals suffering from ICDs experience increasing sense of tension or arousal before committing the act, followed by pleasure, gratification or relief at the time of committing the act. Individuals suffering from ICD often experience impulses which are intrusive, persistent and associated with anxiety or tension. Individuals suffering from paraphilias and nonparaphilic sexual addictions (NPSAs) experience similar increasing senses of tension or arousal before committing the act, followed by pleasure, gratification or relief at the time of committing the act.

Tourette's syndrome is a chronic neuropsychiatric disorder characterized by motor tics and one or more vocal tics beginning before the age of 18 years. The DSM-IV defines a tic as a sudden, rapid, recurrent, non-rhythmic, stereotyped motor movement or vocalization. Tourette's syndrome patients may be able to suppress tics for varying lengths of time, but eventually experience them as irresistible and perform them. Tourette's patients exhibit obsessions resembling OCD obsessions, for example, they often feel the need to perform tics until they are felt to be "just right."

Autism is characterized by difficulties with social interaction, speech and communication, and by a compulsive core. Autistic individuals often display compulsive, repetitive behaviors. First described by Kanner in 1943, autism affects social and communicative abilities and is also characterized by compulsive/repetitive behaviors such as stereotypic complex hand and body movements, craving for sameness, and narrow repetitive interests (American Psychiatric Press, 1994 DSM-IV). In addition, there is high comorbidity with inattention-hyperactivity, impulsivity and aggression, self injury, mood instability, mental retardation and epilepsy, making care for these individuals an even greater challenge for families and institutional settings.

Autism belongs to a group of pervasive developmental disorders (PDD) as characterized by both DSM IV and World Health Organization: International Classification of Diseases, Tenth revision (ICD-10)). In addition to autism, PDDs include Asperger's, ADD, and ADHD. PDDs are typically characterized by multiple distortions in the development of basic psychological functions that are involved in the development of social skills and language, such as attention, perception reality testing and motor movement. In addition, many children diagnosed with Autism, for example, suffer from primary diffuse gastrointestinal problems such as protracted diarrhea and constipation. Although PDDs are currently of unknown etiology, many conventional methods, such as dietary alteration, behavioral modification, and medication, have been utilized for treating individuals suffering from PDD related disorders. Unfortunately, PDD related disorders have no known treatment beyond that which is symptomatic, and these conventional methods have proven unsuccessful in allowing such children and adults to become symptom- or disorder-free.

A child which displays signs of developmentally inappropriate inattention, impulsivity and hyperactivity is typically diagnosed as having ADD and/or ADHD. With these disorders, there can be marked disturbances of organization, distractibility, impulsivity, restlessness, and other disturbances of language and/or social behavior. A combination of psychiatric care and medicine is typically used for treating children with ADD and ADHD.

Behavior modification therapy is often efficacious in treating obsessive-compulsive spectrum disorders, including OCD. However, behavior modification therapy generally requires prolonged periods of treatment. Also, an individual may not respond favorably to behavior modification therapy unless the severe OC spectrum disorder symptoms are first controlled or decreased. Thus, it is often desirable to supplement the initial stages of behavior modification with drug therapy. Preferably, the drug therapy will be one that has a short onset of action, preferably less than two weeks.

Some OC spectrum disorders, such as bulimia nervosa, have been shown to respond to monoamine oxidize inhibitors (MAOIs). Unfortunately, people who use MAOIs are forced to adhere to numerous dietary restrictions and observe special precautions to avoid drug interactions.

OCD has been treated with serotonin reuptake inhibitors (SRIs) such as clomipramine, fluoxetine, fluvoxamine, sertraline and paroxetine. There is also evidence to suggest that Tourette's syndrome, hypochondriasis, anorexia nervosa, and ICDs such as intermitted explosive disorder (IED), kleptomania, pathological gambling, trichotillomania, compulsive shopping, onychophagia and psychogenic excoriation may respond to SRIs. (Goldsmith et al., Conceptual Foundations of Obsessive-Compulsive Spectrum Disorder, in Obsessive-Compulsive Disorder, Richard P. Swinson et al. Editors, The Guilford Press. pages 397-425 (1998).) SRIs have also been used to treat compulsive symptoms in autism. (Hollander, J. Clim. Psychiatry, 58(12): 3-6 (1997).)

Unfortunately, some individuals are refractory to serotonin reuptake inhibitors. Approximately 30 to 50% of individuals do not respond at all to serotonin reuptake inhibitors, while many who do respond do so only partially. Further, serotonin reuptake inhibitors have a slow onset of action and often require eight to ten weeks of treatment to achieve a significant reduction in symptoms. Also, individuals suffering from movement disorders, such as Tourette's syndrome, often desire a drug that can be taken pro re nata (on an as-needed basis).

It was recently discovered that the administration of secretin, a gastrointestinal peptide hormone, to children diagnosed with Autism resulted in ameliorating the symptoms associated with Autism. This finding was published in the article by Horvath et al., entitled Improved Social and Language Skills After Secretin Administration In Patients with Autistic Spectrum Disorders, Journal of the Association for Academic Minority Physician Vol. 9 No. 1, pp. 9-15, January, 1998. The secretin administration, as described in Horvath, was performed as a diagnostic procedure, i.e., to stimulate pancreaticaobiliary secretion during an upper gastrointestinal endoscopy, rather than as a therapeutic procedure. Although the specific mechanism by which the secretin improved the autistic-related symptoms was not specifically identified, Horvath postulated that secretin may have had a direct or indirect effect on the central nervous system. What is important, however, is that this was the first time that gastrointestinal problems of autistic children were linked to a possible etiology in Autism.

Memantine has recently been approved by FDA for the treatment of memory loss in Alzheimer's disease, a neurodegenerative disorder of the nervous system. This approval was based on three randomized placebo-controlled trials that showed significant improvements in cognitive, functional and global endpoints in this population (Tariot et al., JAMA. 2004; 291:317-24, Reisberg et al, N Engl J Med., April 3; 348(14): 1333-41 (2003), Winblad et al., Int J Geriatr Psychiatry, 14(2): 135-46 (1999)). Similar results were seen in two trials in vascular dementia (Wilcock et al., Int Clin Psychopharmacol., 17(6): 297-305(2002), Orgogozo et al., Stroke, 33:1834-9 (2002)). Memantine has been used in Germany for a variety of neurological syndromes and cognitive deficits since 1982 with good tolerability. In animal models, memantine has been shown to prolong the duration of long term potentiation in vivo and to improve learning and memory. (Zajaczkowski et al., Eur J Pharmacol., 296(3): 239-46 (1996)). Neuroprotection has been demonstrated in animals (Danysz et al., Amino Acids., 19(1): 167-72 (2000)) but the clinical data is still pending.

Autism, unlike Alzheimer's disease, is a neurodevelopmental disorder rather than neurodegenerative disease.

There are currently no drugs approved for the treatment of autism and other PDDs. Serotonin reuptake inhibitors have been shown to have some effect on repetitive behaviors. Atypical antipsychotics seem to be effective in the treatment of aggression. Antiepileptic medications may be useful for aggression, especially in children with epileptiform abnormalities. Amantadine, a weak inhibitor of the NMDA glutamate receptor, has been tested in autism. The study showed some improvement in irritability and hyperactivity; however, amantadine has a very weak affinity for this receptor and therefore very high doses would be required to get an adequate effect. Memantine is a newly approved medication for the treatment of cognitive decline in Alzheimer's disease. It has moderate affinity for the NMDA receptor and has properties such as rapid blocking/unblocking abilities that render it very well tolerated.

Thus while numerous degenerative disorders may be treated with a variety of therapies, numerous developmental disorders, for example autism, remain untreatable with modern medicines.

SUMMARY OF THE INVENTION

The invention generally relates to the treatment of behavioral disorders, and more particularly, treatment of compulsive, impulsive, and pervasive developmental disorders. In one embodiment of the present invention, a method of treating an animal having a behavioral disorder is provided comprising administering to the animal an effective amount of a composition comprising memantine or a pharmaceutically acceptable salt thereof, an analog of memantine or a pharmaceutically acceptable salt thereof. In a related embodiment, the animal is a mammal or a human.

In another embodiment of the invention, the aforementioned method is provided wherein the behavioral disorder is a pervasive developmental behavioral disorder. In a related embodiment, the pervasive developmental behavioral disorder is selected from the group consisting of autism, Asperger's syndrome, attention deficit disorder (ADD), and attention deficit hyperactivity disorder (ADHD). In yet another related embodiment, the pervasive developmental behavioral disorder is autism.

In still another embodiment, the aforementioned method is provided wherein the behavioral disorder is obsessive-compulsive spectrum disorder. In a related embodiment, the obsessive-compulsive spectrum disorder is selected from the group consisting of obsessive-compulsive disorder, Tourette's syndrome, body dismorphic disorder, hypochondriasis, eating disorders, impulse control disorders, paraphilias and nonparaphilic sexual addictions, Sydeham's chorea, torticollis, autism and combinations thereof. In still another related embodiment, the obsessive-compulsive spectrum disorder is an impulse control disorder selected from the group consisting of intermittent explosive disorder, kleptomania, pathological gambling, pyromania, compulsive shopping, compulsive buying, repetitive self-mutilation, onychophagia, psychogenic excoriation, trichotillomania and combinations thereof.

In another embodiment of the invention, the aforementioned method is provided wherein the disorders are selected from the group consisting of anorexia nervosa, bulimia, and binge eating. In another embodiment, the disorder is an impulse control disorder from the group consisting of pathological gambling, compulsive buying, sexual compulsion, alcohol and substance use disorders, attention deficit hyperactivity disorder (ADHD), neurological disorders with disinhibition or frontal lobe deficits, bipolar disorder, and childhood onset bipolar disorder.

In yet another embodiment, the invention provides the aforementioned method further comprising administering a serotonin reuptake inhibitor. In a related embodiment, the serotonin reuptake inhibitor is selected from the group consisting of clomipramine, fluoxetine, fluvoxamine, sertraline, paroxetine, citalopram, escitalopram, venlafaxine, mirtazepine, duloxetine and mixtures thereof.

In still another embodiment, the invention provides the aforementioned method further comprising administering an anti-epileptic agent. In a related embodiment, the anti-epileptic agent is selected from the group consisting of valproate, divalproex, gabapentin, topiramate, leviracetam, lamotrigine, carbamazapine, oxcarbamazepine, tiagabine, zonisamide, clonzaepam, pregabalin, zarontin and mixtures thereof.

In another embodiment of the invention, the aforementioned method is provided further comprising administering a stimulant or non-stimulant of attention. In a related embodiment, the stimulant or non-stimulant of attention is selected from the group consisting of dextroamphetamine, methylphenidate, adderall, adderall XR, concerta, focalin, and strattera.

In yet another embodiment, the aforementioned method is provided further comprising administering an a atypical antipsychotic. In a related embodiment, the atypical antipsychotic is selected from the group consisting of risperidone, olanzepine, quetiapine, ziprasidone, and aripiprazole. In still another embodiment, the aforementioned method is provided further comprising administering a cholinergic enhancer. In a related embodiment, the cholinergic enhancer is selected from the group consisting of aricept (donepezil), excelon, reminyl (galantamine), and mestinon.

In still another embodiment of the invention, the aforementioned method is provided wherein the administration produces at least a rating of 2 on the Clinical Global Impression Improvement Scale-AD, or an improvement on the Vineland Adaptive Behavior Scale, ABC (Aberrant Behavior Checklist), PDD-BI Scale, YBOCS, CY-BOCS, ADOS, language scales, attention scales. In particularly preferred embodiments a CGI-improvement of 1 (denoting that the symptoms are very much improved).

In yet another embodiment, the aforementioned method is provided wherein the memantine is administered at a daily dose of 0.01 to 500 mg/kg. In a similar embodiment of the invention, the memantine is administered at a daily dose of between about 1 mg/day and about 50 mg/day. In a related embodiment, the memantine is administered at 5 to 10 mg twice per day.

In another embodiment of the invention, a method for treating an individual having an autistic disorder comprising administering to the individual memantine in an amount effective to improve a symptom of the disorder is provided. In related embodiments, the symptom comprises an impairment in making eye contact with another individual, a lack of social interaction with another individual, a delay in or lack of spoken language, a repetitive pattern of behavior such as arm flapping, hyperactivity, cognitive impairment, and/or attention deficit.

In yet another embodiment, the aforementioned method is provided wherein the memantine is administered at a daily dose of 0.01 to 500 mg/kg. In a related embodiment the memantine is administered at a daily dose of between about 1 mg/day and about 50 mg/day. In still another related embodiment, the memantine is administered at 5 to 10 mg twice a day.

DETAILED DESCRIPTION OF THE PREFERRED EMBODIMENTS

As discussed in the background, there exists a significant need for new therapies of PDD. The present application provides treatment of PDDs with memantine. In a preferred embodiment, autistic patients are treated with memantine.

Autism is a developmental disorder characterized by repetitive behaviors and restricted interests, and social and language deficits. When all forms of the syndrome are taken into consideration, autism affects up to 60/10,000 individuals. Recently there is intriguing evidence that the glutamate system is affected in autism. Patients with autism have higher blood levels of glutamate than unaffected individuals. Abnormalities of the glutamate system are seen in studies of brains of deceased autistic patients. Genetic studies have shown mutations of glutamate genes in autistic subjects.

The invention provides methods for treating a patient diagnosed as suffering from an OC disorder such as a PDD described herein above (e.g., autism, Tourette's syndrome, body dismorphic disorder, hypochondriasis, eating disorders, impulse control disorders, paraphilias and nonparaphilic sexual addictions, Sydeham's chorea, torticollis, attention deficit disorder, pathological gambling, compulsive buying, sexual compulsion, alcohol and substance use disorders, attention deficit hyperactivity disorder (ADHD), neurological disorders with disinhibition or frontal lobe deficits, bipolar disorder, anorexia nervosa, bulimia, intermittent explosive disorder, kleptomania, pathological gambling, pyromania, compulsive shopping, compulsive buying, repetitive self-mutilation, onychophagia, psychogenic excoriation, trichotillomania, binge eating and childhood onset bipolar disorder). As discussed herein throughout those of skill in the art of clinical psychiatry are aware of a variety of methods for diagnosing these disorders, and any conventional diagnostic method can be used in conjunction with the invention.

The treatment method of the invention entails administering to a patient diagnosed as having a OC disorder a pharmaceutical composition containing a therapeutically effective amount of memantine either alone or in combination with another therapeutic intervention, e.g., use of an agonist of the glycine site of the NMDA receptor, a glycine uptake inhibitor, a serine uptake inhibitor or behavioral modification therapy.

Memantine Therapy

Amantadine was shown to have NMDA non-competitive inhibitor activity at doses routinely used for Influenza and Parkinson disease (Kornhuber et al, J Neural Transm Suppl., 43: 91-104 (1994)), without having any psychomimetic side effects. On the basis of that, a double blind placebo controlled trial of Amantadine was carried out in autistic children. While it was tolerated, it was noted to have a modest, at best, effect on irritability and hyperactivity. This effect may be due to amantadine's low affinity for the NMDA receptor.

Memantine is also a non-competitive NMDA inhibitor. It has, however, moderate affinity for the receptor, with strong voltage dependency and rapid blocking and unblocking properties. (Mobius, Int J Geriatr Psychiatry, 18(Suppl 1): S47-54 (2003)). It seems to block the sustained activation at micromolar concentrations of glutamate under pathological conditions but to rapidly leave the NMDA channel upon transient physiological activation at milli-molar concentrations of synaptic glutamate (Parsons et al., Amino Acids. 19(1): 157-66 (1993)). It occupies approximately five out of the six ion channels in the receptor, allowing the sixth one to remain free under resting conditions and available for physiological transmission. (Blanpied et al., J Neurophysiol., 77(1): 309-23 (1997)). These features are thought to form the basis for the lack of psychomimetic side effects seen with PCP and PCP-like substances.

Memantine undergoes little metabolism, with the majority (57-82%) of an administered dose excreted unchanged in urine. The remainder is converted primarily into three metabolites: the N-gludantan conjugate, 6-hydroxy memantine, and 1-nitroso-deaminated memantine. These metabolites have minimal NMDA receptor antagonist activity. The hepatic microsomal CYP450 enzyme system does not play a significant role in the metabolism of memantine. Memantine has a terminal elimination half life of about 60-80 hours. Renal clearance involves active tubular secretion.

In the present invention, it is shown that memantine may be used in the treatment of autism and other PDDs discussed herein above.

Disorders Amenable to Memantine Treatment

Disorders contemplated by the present invention to be amenable to treatment with memantine include, but are not limited to, behavioral disorders, pervasive behavioral disorders, autism, Asperger's syndrome, obsessive-compulsive spectrum disorder, Tourette's syndrome, body dismorphic disorder, hypochondriasis, eating disorders, impulse control disorders, paraphilias and nonparaphilic sexual addictions, Sydeham's chorea, torticollis, intermittent explosive disorder, kleptomania, pathological gambling, pyromania, compulsive shopping, compulsive buying, repetitive self-mutilation, onychophagia, psychogenic excoriation, trichotillomania, anorexia nervosa, bulimia, binge eating, pathological gambling, compulsive buying, sexual compulsion, alcohol and substance use disorders, attention deficit disorder (ADD), attention deficit hyperactivity disorder (ADHD), neurological disorders with disinhibition or frontal lobe deficits, bipolar disorder, and childhood onset bipolar disorder. In particularly preferred embodiments, the methods of the present invention employ memantine for the treatment of autism. The following discussions provide measurements for diagnosing autism and prognostic determinations of the efficacy of a given therapeutic regimen.

Rating Instruments for Diagnosing Autism

A variety of methods may be used to diagnose an OC disorder such as autism and to monitor the efficacy of the memantine-based therapy. Many of the general diagnostic methods are described in e.g., U.S. Pat. No. 6,387,956; U.S. Pat. No. 6,420,351; U.S. Pat. No. 6,410,527; U.S. Pat. No. 6,632,429; U.S. Pat. No. 6,716,416; U.S. Pat. No. 6,667,297; and U.S. Pat. No. 6,512,010. The following discussion provides exemplary such methods that may be used to diagnose the disorders and monitor the therapies administered according to the present invention.

A. Epidemiology and Phenomenology

There are 32 large surveys of autism published in English. These surveys vary significantly in sample size, approach to identifying subjects, screening methodology and the diagnostic instruments employed. (Fombonne, Psychological Medicine, 29:769-786 (1999. The diagnostic criteria have also changed overtime from Kanner's criteria in the 1960s to DSM-IV and ICD-10 in the 1990s. These latter two indices for characterizing PDDs are well known to those of skill in the art and are typically used to assess a given disorder.

When prevalence data is limited to studies after 1937, the prevalence is estimated to be 10/10,000. However, recent epidemiological surveys that included patients with the diagnosis of Asperger's Syndrome and PDD-NOS, have reported rates in the order of 60/10,000. The incidence of mental retardation is estimated to be 19.3% in classical autism (Fombonne supra). However, the number of intellectually intact subjects is higher among those with a diagnosis in the autistic spectrum but not meeting criteria for classical autism (Chacrabarti & Fombonne, JAMA, 285:3093-9 (2001)). The ratio of male to female is approximately 4:1. For individuals in the normal intellectual range this increases to 6:1, but is only 1.7:1 for those with significant MR. (Fombonne supra). There is no correlation between socioeconomic status and autism in the studies conducted after 1980. Rates of medical conditions associated with autism vary greatly among studies. Epilepsy, Down syndrome, Fragile X syndrome, sensory deficits, congenital rubella and cerebral palsy have all been evaluated in this population. Only 6% of autism cases have been associated with another medical condition that is potentially linked to the etiology of autism. Of the above disorders, the most frequent is epilepsy with a co-prevalence rate of up to 42%.

There are three core dimensions identified by the DSM-IV: social deficits, compulsive/repetitive behaviors and restricted interests, and speech/communication deficits. The most characteristic deficit in autism is the impairment of social interaction which often presents itself as the inability to form relationships and to reciprocate. The social deficits in autism are found in basic socio-communicative behaviors, i.e. lack of eye contact and facial expression, in contexts where coordination of these behaviors results in a 'social-cognitive event', such as pointing, and in reciprocal relationships. Impairments in communication include both nonverbal language, such as pointing, nodding and showing and verbal language. For verbal autistic persons, there is a multitude of deficits reported, including deficits in pragmatics, variable expressive and receptive difficulties, semantic impairments, and occasionally phonology abnormalities. About one-half of autistic children are considered to be non-verbal, but this number seems to be decreasing with early intervention programs. Compulsive/repetitive behaviors include craving for sameness, the need for things to be 'just so' or stereotyped and repetitive behaviors, and unusual preoccupations and activities such as recalculating statistics and memorizing bus symmetrical, routes.

In the present invention, it is contemplated that the social and communication deficit dimensions of autism will be assessed for change. The primary outcome measures for the social dimension will be the Aberrant Behavior Checklist (Aman et al., Am J Ment Defic., 89(5):485-491 (1985)). Similarly, for the language deficit domain, the Controlled Oral World Association test, COWA, and the Peabody Picture Vocabulary test (Randolph, J Clin Exp Neuropsychol., 20(3): 310-9 (1998) are contemplated to be useful for assessing autism.

B. Associated Symptoms

Aggression, both self- and other-directed, and impulsivity are commonly associated with autism (Weller et al., J Clin Psychiatry, 60 (suppl 15): 5-11 (1999), Jaselskis et al., J Clin Psychopharmacol., 12(5):322-7 (1992)). Self-injurious behavior, considered to be one form of aggression has a prevalence of 25-43% in the autistic population. (Tsai, J Aut Dev Disord, 159-163 (1996), Chung, et al, J Aut Dev Disord, 20:221-232 (1990); Simons, J Aut Child Schizophrenia, 4:1-10 (1974)). Of child patients with autism entered into a placebo-controlled, double-blind study of fluoxetine approximately 50% presented with aggressive behavior as a significant comorbid symptom. There is also evidence of increased expression of impulsivity trait in relatives of autistic probands (Murphy et al., Psychol Med., 30(6):1411-24 (2000).

In the present invention, the effect of memantine on impulsive aggression is assessed using the Irritability subscale of the Aberrant Behavior Scale (Aman et al, supra) and the Overt Aggression Scale Modified (OASM) (Coccaro et al, J Neuropsych Clin Neurosci., 3(2):S44-S51 (1991).

There is an association between mental retardation and autistic disorder, with up to 75% of autistic individuals functioning in the retarded range (Freeman, J Aut Devel Dis., 27: 641-651 (1997); Rapin, New England J of Med., 337: 97-104 (1997)). In addition memory deficits have repeatedly been reported with some evidence pointing to limbic-prefrontally controlled episodic memory being the most affected. (Shalom B, Cortex, 39:1129-38 (2003)).

IQ and functional ability testing will be conducted for each subject to establish an index of mental retardation and impairment of functioning. IQ will be assessed via the WAIS-III (Wechsler D. Wechsler Adult Intelligence Scale—Third Edition. The Psychological Corporation, Harcourt Brace & Company, 1997). The Vineland Adaptive Behavior Scale (used in e.g., Loveland et al., J Aut Dev Disord, 1998; 28(4): 287-302; Dunlap et al., Am Ann Deaf. 1990; 135:384-8; Freeman et al., Adolescent Psychiatry, 1988; 27(4): 428-429; Vineland et al., 1984) will be used to measure functional ability, and will be conducted at the beginning and end of subjects' participation to record any change in functional ability. Memory function will be assessed and monitored by the Repeatable Battery for the Assessment of Neuropsychological Status (Randolph, J Clin Exp Neuropsychol., 20(3): 310-9 (1998)) and the Visual Memory Span Subtest of the Wechsler Memory Scale-Revised (the Wechsler memory scale is designed to assess learning, memory, and working memory).

Other comorbid conditions not to be assessed with this protocol include affective instability, hyperactivity, epilepsy and a variety of medical syndromes and disorders.

C. Rating Instruments

Numerous rating instruments are contemplated by the present invention for use in initially diagnosing autism or other PDD and for assessing the efficacy of the given therapy. These instruments include:

1. DSM-IV: This is the standard psychiatric nomenclature currently in use in the U.S.A., and it provides operationalized inclusion and exclusion criteria for autistic disorder (Diagnostic and Statistical Manual of Mental Disorders, Fourth Edition, Text Revision. Washington, D.C.: American Psychiatric Press, 2000).

2. Autism Diagnostic Interview-Revised (ADI-R): (Rutter M, Lord C, LeCouteur A: Autism Diagnostic Interview-Revised (ADI-R) Third Edition. Department of Psychiatry, University of Chicago, 1994b). The ADI-R is a semi-structured psychiatric interview designed for the study of autism and related disorders, typically administered to the subject's primary caretaker/family member. The instrument differentiates autistic from non-autistic mentally handicapped individuals age 3 to young adulthood and provides convergent validation of symptomatology. The ADI-R employs a diagnostic algorithm based upon ICD-10 criteria specifically keyed into the core dimensions of autism—social interaction impairments, speech and communication deficits, and repetitive behavior (Lord et al., J Aut Devel Dis., 24(5): 659-685 (1994)), based on factor analyses resulting from extensive study of the psychometric properties of the instrument (Lord et al., supra). Administration time is approximately 2 hours.

3. Autism Diagnostic Observation Schedule-Generic (ADDS-G): (Lord C, Rutter M, DiLavre P C. Autism Diagnostic Observation Schedule—Generic (ADOS-G). San Antonio, Tex.: Psychological Corp. 1998). The ADOSG has now replaced the former Autism Diagnostic Observation Schedule (ADOS) and the Pre-Linguistic Autism Diagnostic Observation Schedule (PL-ADOS). This instrument was developed as a companion instrument for the ADI-R. The ADDS-G is a standardized protocol for the observation of social and communicative behavior in children, adolescents and adults who are suspected of having an autism spectrum disorder. The ADDS-G consists of standard activities that allow the examiner to observe the occurrence or absence of behaviors that have been identified as important to the diagnosis of autism spectrum disorders across developmental levels and chronological ages.

There are four modules to the ADOS-G. Module 1 is intended for children who are nonverbal or do not consistently use three-word phrases. Module 2 is appropriate for children with expressive language skills between 30 to 47-month level (as assessed by the Vineland Adaptive Behavior Scale). Modules 3 and 4 are intended for individuals with expressive language skills at a 48-month level or higher. Module 3 has a greater emphasis on the use of toys, thus appropriate for children and preadolescents. Module 4 focuses more on interview questions. The instrument provides a series of structured and semi-structured "presses" for social interaction and communication that can be scored. Ratings are completed immediately following administration. Cutoff criteria are ascertained using a diagnostic algorithm. Administration time is approximately 45 minutes.

4. Wechsler Adult Intelligence Scale-III: (Wechsler D. Wechsler Adult Intelligence Scale—Third Edition. The Psychological Corporation, Harcourt Brace & Company, 1997). This is an instrument that gives information about overall intellectual functioning. It is considered the "gold standard" of intelligence testing. It is composed of 11 subtests: 6 verbal and 5 performance oriented. The instrument has good split-test and test-retest variability. Administration time is 1-2 hours.

5. Clinical Global Impression Improvement (CGI)-AD (Guy W. ECDEU assessment manual for psychopharmacology. Revised. NIMH Publication DHEW Publ No (adm.) 76-388. Bethesda, Md.: National Institute of Mental Health, 1976; 217-222). This is a standard rating scale with 7-point global severity and change scales which has been modified for Autistic Disorder. A rating of 2 is given when there is a substantial reduction in symptoms so that a treating clinician would be unlikely to readily change treatment. A rating of 1 is reserved for patients who become virtually symptom-free. A rating of 3 (minimally improved) on the CGI is defined as slight symptomatic improvement that is not deemed clinically significant; patients with such improvement will not be continued into maintenance. Administration time is approximately 2 minutes.

The patients that are to receive the memantine-based therapies should have substantial symptom severity according to at least one of the afore-mentioned tests for assessing autism that suggests a new treatment would be worthwhile. Patients will need to meet Autism Diagnostic Interview and Autism Diagnostic Observation Schedule criteria for the diagnosis of autism that includes minimum cutoff scores on all three core dimensions of the disorder. In addition, subjects will meet a cutoff score of "4" (moderately ill) on the Clinical Global Impression of severity for Autistic Disorders (CGI-AD) to be included in the study. Arnold et al., The Autism RUPP Network, J of Autism and Devel. Disorders, 30(2):99-111 (2000) have argued that the CGI severity scores should be anchored around a score of "3" (mildly ill) for uncomplicated autism, that is, autism that is unaccompanied by secondary behaviors (such as the associated features targeted in this study). Arnold et al. suggest that they would expect greater range of treatment change on the secondary behaviors than on core autism symptoms, and wish to reserve the four highest severity designations ("4" moderately ill to "7" among the most extremely ill) for patients with severe comorbid conditions. Although studies are preliminary, change in core autism symptomatology has been demonstrated in treatment trials (DeLong, Dev Med Child Neuro., 40:551-562 (1998); McDougle, Arch Gen Psychiatry, 53:1001-1008 (1996); Awad. Can J Psych., 41:361-366 (1996); Markowitz, Journal Clin Psychopharmacology, 12: 27-31 (1992); Cook, et al., J Am Acad Child Adolesc Psychiatry, 31:739-745 (1992); Todd, J Aut Dev Disord., 159-163 (1991); Ghazziuddin et al., J Am Acad Child Adolesc Psychiatry, 30(3):508-9 (1991); Mehlinger et al., J Am Acad Child Adolesc Psychiatry, 29:985 (1990)). Therefore, it is desirable to capture response to treatment in the core autism symptoms dimensions as well as associated features. Severity of core symptomatology may in fact be a predictor of treatment response. Additionally, as separate measures specifically designed to assess treatment change in "secondary behaviors" may be used, it is contemplated that the Clinical Global Impression Scale is best used as an assessment of global change, capturing the entire clinical picture of a subject.

6. Aberrant Behavior Checklist (ABC) (irritability) (Aman et al., Am J Ment Defic., 89(5):485-491 (1985)). The Aberrant Behavior Checklist assesses drug and other treatment effects on mentally retarded individuals. It consists of a five factor scale comprising 58 items. An irritability section will be used to assess social relatedness. While the internal consistency, validity and test-retest reliability were reported to be very good, inter-rater reliability was moderate (Aman et al, supra). The ABC will be filled out by an informant, and then reviewed by the treating psychiatrist. Administration time is approximately 10 minutes.

7. Repeatable Battery of the Assessment of Neuropsychological Status (Randolph, supra). This instrument helps determine the neuropsychological status of adults up to age 89 that are known to have neurological or neuropsychiatric difficulties such as dementia, trauma, and schizophrenia. It can provide a sampling of different types of memory and some other cognitive areas. It has two parallel forms, ideal for measuring change in the client's neuropsychological status over time. It has been shown to be a validated instrument with good sensitivity and reliability. Test retest reliability was shown to be 0.8 in schizophrenia. The test takes approximately 30 minutes.

8. Aberrant Behavior Checklist (ABC) (lethargy/social withdrawal section) (Aman et al., supra). The Aberrant Behavior Checklist assesses drug and other treatment effects on mentally retarded individuals. It consists of a five-factor scale comprising 58 items. Lethargy/Social Withdrawal section will be used to assess social relatedness. While the internal consistency, validity, and test-retest reliability were reported to be very good; inter-rater reliability was moderate (Aman et al, supra). The ABC will be filed out by an informant, and then reviewed by the treating psychiatrist. Administration time is approximately 10 minutes.

9. Controlled Oral Word Association test: (Benton et al, supra). The purpose of this test is to evaluate the spontaneous production of words beginning with a given letter. It has been shown to have near perfect inter-rater variability, and the retest reliability after 19-42 days in adults is 0.88. Concurrent validity has been established is several studies. Normative data exists for variable educational levels and ages. Administration time is 5-10 minutes.

10. Visual Memory Span Subtest of the VMS-III (Wechsler, 1987, supra) This is a subtest of the Wechsler Memory Scale-III, a well validated and comprehensive instrument. The particular subtest has two parts: tapping forward and tapping backward. It will provide additional information regarding visual memory in this population. It requires 5-10 minutes for administration.

11. Overt Aggression Scale Modified (OAS-M) (Coccaro et al, supra). This scale is a modification of the original Overt Aggression Scale (OAS) designed by Yudovsky and colleagues for objectification of single inpatient events of behavioral irritability, as well as the Schedule for Affective Disorders and Schizophrenia (SADS). The Modified version by Coccaro et al. is designed for outpatient use and for assessment of behavior over a one week period. The OAS-M consists of 3 domains: Aggression, Irritability, and Suicidality. For Aggression there are 4 subscales of behavior: Verbal Aggression, Aggression Against Objects, Aggression Against Others, and Auto Aggression (aggression against self). Within each category, severity of an event receives a scaled score (higher score for more impulsive/aggressive behaviors) which is then multiplied by the frequency of this event for the week. The OAS-M has been demonstrated to be sensitive to change in impulsive/aggressive behaviors in patients with personality disorders during medication trials. The Aggression domain of this instrument to will only be used to assess aggression and self-injurious behavior. Intra-class correlations for the Total Aggression and Irritability subscales are high (0.91). Inter-correlations among OAS-M subscales are moderate and statistically significant. Administration time is approximately 10 minutes.

12. Vineland Adaptive Behavior Scale (Vineland et al., supra). The Vineland Scale is a semi-structured informant interview that assesses subjects' daily functioning. It is typically administered to a caretaker/family member (Dunlap and Sands, Am Ann Deaf, 135:384-8 (1990); Dykens et al., Am Acad Child Adolesc Psychiatry, 28:427-30 (1989); Voelker et al. Ment Retard., 28:305-9 (1990)). The scale has been revised and standardized in retarded and normal populations (Sparrow et al., Vineland Adaptive Behavior Scales. Circle Pines, Minn.: American Guidance Service, 1984) based on a representative national sample. In addition, the Vineland has been recently normalized for the autistic population (Carter et al, J Aut Dev Disord., 28(4):287-302 (1998)). This scale has been found to assess social deficits in autism (Loveland and Kelley, Am J Men Retard., 93:84-92 (1988); Loveland and Kelley, Am J Men Retard., 96: 12-20 (1991); Rodriguez et al., J Aut Dev Dis., 21:187-196 (1991) and relative strengths in daily living skills (Carter et al, J Aut Dev Disord., 28(4):287-302 (1998)). Items are classified under four major adaptive domains: communication, daily living skills, socialization and motor skills. The Vineland yields a summary score referred to as the Adaptive Behavior Composite, which is predictive of social adaptation and long-term outcome (Freeman et al., Adolescent Psychiatry, 27(4): 428-429 (1988)).

13. Peabody Picture Vocabulary test-III (Dunn & Dunn, Peabody picture vocabulary test. Circle Pines, Minn.: American Guidance Service, 1981). This instrument is designed to assess auditory comprehension of picture names. The third version provides gender and ethnic balance and has been re-standardized for the age range from 2.5 years to 90 years of age. It is well validated and has good sensitivity and reliability. It requires 10-20 minutes for administration.

D. Quality Control and Data Analyses

Medical treatment: will be administered by board certified or eligible psychiatrists or neurologists who are currently in, or have completed, research and clinical fellowships in psychopharmacology of autism and compulsive spectrum disorders or child psychiatry.

Inter-rater reliability: Ideally, a group of psychiatrists, psychologists, and independent evaluators have worked together for years and have developed a high degree of inter-rater reliability. Investigators of this study have undergone an intensive training seminar with the developers of the Autism Diagnostic Interview-Revised. Raters established reliability with expert/developers of the ADI-R both in on-site interviews with autistic children and their caretakers and in videotaped interviews reviewed by developers of the ADI-R. Acceptable inter-rater reliability kappas at the end of training were at least 0.85 between the experts. Raters have been extensively trained to achieve consistency for rating scales used in the study.

Monitoring treatment compliance: An inventory of medications will be taken at each visit. Medications will be dispensed to patients by the parent, guardian, or a responsible adult to maximize compliance.

Data Analysis: Analyses will be carried out to determine whether there are baseline differences between treatment groups on the following potential covariates: age, ethnicity, intelligence level, severity of autism (CGI-AD), aggression (assessed by the ABC); memory (assessed by the RBANS) or language abilities (assessed by the COWA). Chi square analyses will be used for discrete variables and ANOVA for continuous variables. A variable will be used as a covariate if there is a baseline difference between groups.

Primary Analyses: The Independent Evaluator (IE) ratings will be used in the primary analyses. The primary analysis will be the intent-to-treat analysis, which will include all subjects randomized into the study with last observation carried forward. An intent-to-treat analysis controls for differential dropout biases in the two groups. A separate analysis of dropouts will be conducted to determine whether this group differed in demographic or potential predictor variables from the subjects that remained in treatment Each hypothesis is a comparison of memantine vs. placebo treatment on dependent variables in different domains. In hypothesis 1, the domain is global autism improvement (CGI-I-AD); in hypothesis 2, the domain is language deficits (COWA); in hypothesis 3, the domain is social reciprocity (ABC); in hypothesis 4, the domain is memory deficits (RBANS); and in hypothesis 5, the domain is aggression and irritability (ABC). The scaled dependent variables will be tested using analysis of covariance with covariates being the baseline measure rated by the IE, and any other covariates as described above. For hypothesis 1, the dependent variable will be the CGI-I-AD and the covariate is the CGI-S-AD. If ethnicity is a covariate, its four categories will be used to define three dummy-coded dichotomies. For hypothesis 6, regression analysis will be performed. The interaction of the treatment with the two haplotypes of the GRIK2 gene may also be tested.

Each measure of each hypothesis will be tested at the significance level 0.05. If any result is significant, the conclusion will be that memantine differs from placebo and that there is a difference in the respective hypothesis and domain. Although hypotheses are directional, all tests of significance will be two-sided.

Secondary Analyses: (Effect of memantine vs. placebo on secondary outcome measures) In addition, each secondary outcome measure will be tested in a similar fashion as the primary analyses. Please refer to page 20 for a list of secondary outcome measures in each domain. For each secondary measure, the level of significance will be 0.05. Although hypotheses are directional, all tests will be two sided.

Power Analyses: A primary goal of this exploratory grant is to generate data upon which a power analysis can be based for future large-scale clinical trials with memantine in autism.

Power analyses follow Cohen (Statistical power analysis for the behavioral sciences (2nd ed.). Lawrence Erlbaum Associates (pub), New York, 1988), who proposed "small," 'medium," and "large" effect sizes for a variety of statistical procedures. For Student's t-test, these are differences between group means of 0.2, 0.5, and 0.8 standard deviations, respectively. There are currently no other studies of memantine in the autism population or in other similar populations to base the power analysis on. For 15 subjects per group, if the effect size were 1.6 found by McDougle et al (Arch Gen Psychiatry, 53:1001-1008 (1996) in a study of Fluvoxamine vs. placebo, the power would be 0.99. However, if the effect size were smaller, such as 0.8, the power would only be 0.56. Since this is a pilot study, it is anticipated that the sample sizes may be too small for a definitive conclusion, particularly if the results are null, but it is hoped that these results will be sufficiently favorable to justify a larger study.

E. Combination Therapy

The present invention also contemplates the use of memantine in combination(s) with other therapeutics to treat patients suffering from one or more of the disorders described herein. By way of example, other therapeutics that may be administered with memantine include, but are not limited to, serotonin re-uptake inhibitors, NMDA inhibitors, anti-epileptics, attention stimulants/non-stimulants, atypical antipsychotics, and cholinergic enhancers. The memantine also may be used in combination with behavioral therapy.

Many individuals suffering from OC spectrum disorders respond favorably to behavior modification therapy. However, with some individuals the OC spectrum disorder symptoms may be so severe that they interfere with the initiation of behavior modification therapy. For example, an individual with extremely severe OCD directed toward contamination may be reluctant to leave his domicile in order to obtain behavior modification therapy. Such an individual would benefit from a drug therapy which was able to quickly control or decrease the severity of the OCD symptoms, thereby rendering the individual more willing to obtain behavior modification therapy. The rapid onset of response to memantine allows for an individual's OC spectrum disorder symptoms would provide such a benefit. The memantine treatment may be initiated prior to or along with the initiation of behavior modification therapy. Individuals who have already initiated behavior modification therapy may also be treated with memantine. This may be particularly beneficial if it appears the severity of the OC spectrum disorder symptoms is interfering with the behavior modification therapy.

In one preferred embodiment, the individual suffering from an OC spectrum disorder is treated with memantine during or prior to initiation of behavior modification therapy or other therapy for OC spectrum disorders. Preferably, the memantine therapy is initiated prior to the initiation of the behavior modification therapy, more preferably at least about 2 days prior to the initiation of the behavior modification therapy, even more preferably at least about 7 days prior to the initiation of the behavior modification therapy. Suitable forms of behavior modification therapy are known in the art, and include exposure and response prevention, thought stopping, saturation therapy, stimulus control therapy, or modeling therapy.

Another surprising advantage of the rapid onset of response of memantine is the treatment of the symptoms of OC spectrum disorders, particularly autism, on an as-needed basis. As used herein, "as-needed basis" is intended to refer to a dosing regime wherein the individual takes a pharmacological agent at a time and at a level sufficient to control symptoms as desired. Although memantine may be prescribed according to a schedule, such as, for example, 100 mg 4 times a day, there may be occasions when an as-needed basis is preferred.

For example, an individual with an OC spectrum disorder may desire to control or decrease symptoms for specific events or occasions. Autistic patients may be given the as-needed dose of memantine before exposure to a stress-inducing situation. A Tourette's syndrome patient may wish to take memantine prior to an event such as taking a class or giving a speech, while a bulimia nervosa or BED patient may wish to take memantine before meals or particular situations which usually lead to binge eating or purging. An individual with compulsive buying may take memantine before going near stores while an individual with pathologic gambling may take memantine before exposures to triggers that lead to gambling. OCD patients may wish to take an as-needed dose of memantine before exposure to a stress-inducing situation. For example, a patient with contamination obsessions and/or cleaning compulsions may take memantine prior to cleaning a bathroom, while a patient with obsessions of harm may take memantine prior to caring for children.

Oral administration of an effective dose of memantine, preferably memantine hydrochloride, at least about one hour prior to the point in time at which the decrease of symptoms is desired will result in an effective decrease in symptoms. The memantine will decrease the symptoms for a period of up to about six hours. Generally, the as-needed dose will be from about 50 to about 400 mg of oral memantine.

If desired, the memantine treatment may be supplemented with a SRI, provided the individual responds at least partially to SRIs. Preferably the SRI is selected from clomipramine, fluvoxamine, fluoxetine, sertraline, and paroxetine, more preferably, the SRI is a SSRI selected from the group consisting of fluvoxamine, fluoxetine, sertraline and paroxetine. Generally, the average dose of the serotonin reuptake inhibitor is from the range of from about 10 to about 200, more preferably from about 10 to about 40, mg daily. Preferably the SRI is administered orally.

If long-term maintenance therapy on SRIs are desired, the individual may initially be treated with a combination of SRI and memantine in order to obtain a rapid decrease in the OC spectrum disorder symptoms. After sufficient time has passed for the SRI response to occur, generally from about 8 to 10 weeks, the level of memantine may be slowly tapered off until the individual is being treated only with the SRI.

Examples of serotonin re-uptake inhibitors that are contemplated by the present invention include, but are not limited to, clomipramine, fluoxetine, fluvoxamine, sertraline, paroxetine, citalopram, escitalopram, venlafaxine, mirtazepine, duloxetine and mixtures thereof.

Examples of anti-epileptic agents that are contemplated by the present invention include, but are not limited to, valproate, divalproex, gabapentin, topiramate, levinacetam, lamotrigine, carbamazepine, oxcarbamazepine, tiagabine, zonisamide, clonzaepam, pregabalin, zarontin and mixtures thereof.

Examples of attention stimulants/non-stimulants that are contemplated by the present invention include, but are not limited to, dextroamphetamine, methylphenidate, adderall, adderall XR, concerta, focalin, and strattera.

Examples of atypical antipsychotics that are contemplated by the present invention include, but are not limited to, risperidone, olanzepine, quetiapine, ziprasidone, and aripiprazole.

Examples of cholinergic enhancers that are contemplated by the present invention include, but are not limited to, aricept (donepezil), excelon, reminyl (galantamine), and mestinon.

F. Pharmaceuticals

Prodrug refers to a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing pro drugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

Memantine used in the practice of a method of the invention may be formulated into pharmaceutical compositions comprising a carrier suitable for the desired delivery method. Suitable carriers include any material which, when combined with memantine, retains the function of memantine and is non-reactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Therapeutic formulations of memantine are prepared for storage by mixing memantine having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Memantine is administered by any suitable means, including parenteral, subcutaneous, intraperitoneal, intrapulmonary, and intranasal, and, if desired for local treatment, intralesional administration. Parenteral infusions include intravenous, intra-arterial, intraperitoneal, intramuscular, intradermal or subcutaneous administration. In addition, memantine is suitably administered by pulse infusion, particularly with declining doses of memantine. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site.

Compositions of the present invention can be in the form of, for example, granules, powders, tablets, capsules, syrup, suppositories, injections, emulsions, elixirs, suspensions or solutions. The instant compositions can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

The memantine may be administered in any suitable form, including tablets, liquids, timed release capsules, in the form of a candy such as a lollipop, sprinkles which are mixed with soft foods, sublingual dosing, transepidermal patches, subcutaneous sustained release devices, nasal sprays, rectal suppositories and injections. When a sustained release is desired preferred forms are timed capsules, transepidermal patches, and subcutaneous sustained release devices. When a quick response is desired preferred forms are sublingual dosing and injection. For children, geriatric patients, and patients who might have trouble swallowing or compliance problems, preferred forms are candy, sprinkles, rectal suppositories and liquids.

As used herein, "an effective amount" refers to the minimum amount required to decrease the severity of the OC spectrum disorder symptoms. An individual preferably exhibits a decrease in Y-BOCS or other scores for the assessment of such a disorder after about 14 days of treatment, more preferably after about 7 days of treatment. Even more preferably, the individual experiences a decrease in compulsive behavior after about 2 days of treatment.

Preferably the memantine is in the form of a hydrochloride. Generally, the individual is treated with a total of from about 50 to about 400, preferably from about 100 to about 400, mg of memantine per day. In one embodiment, the memantine dose may be divided into from about 2 to about 5, preferably from about 2 to about 3, individual doses a day, with each individual dose being from about 50 to about 200, more preferably from about 50 to about 100, mg of memantine. In one embodiment the individual is treated with from about 50 to about 100 mg of memantine two to three times a day. Generally two to three individual doses a day are preferred from efficacy, tolerability and compliance aspects, however, more severely affected individuals may require from four to five individual doses a day to control symptoms. Those of skill in the art are aware of formulations and methods of administering memantine for the therapeutic intervention of disorders such as Alzheimer's disease (Rive et al., Int J Geriatr Psychiatry. 2004 May; 19(5):458-64); vascular dementia (Winblad et al., Lancet Neurol 2002; 1:469); ischemic stroke (Culmsee et al., Stroke. 2004:35:1197:202); Parkinson's disease Merello et al., Clin Neuropharmacol. 1999; 22:273-6); Huntington's disease (Palmer, Curr Drug Targets. 2001; 2:241-71); retinal ganglion injury (Lipton, Surv Ophthalmol. 2003; 48:S38-46); cochlea (Oestreicher et al., ORL J Otorhinolaryngol Relat Spec. 1998:60:18-21); MS-nystagmus in multiple sclerosis (Stark et al., J Neurol 1997; 244:9-16); treatment of severe spastic and extrapyramidal movement disorders in combination with stereotaxic surgery. (Mundinger et al., Nervenarzt. 1985 February;56(2):106-9); drug resistant dyskinesia (Hanagashi et al., Mov Disord 2000; 15:1016-7); painful peripheral neuropathy (Kirby et al., Pain Med 2002; 3:182); modulation of glutamate systems in addiction (Bisaga et al., Psychopharmacology (Berl) 2001; 157:1-10). Each of the foregoing documents is incorporated herein by reference as providing a general teaching of methods and routes of administration of memantine that are well known to those of skill in the art. Memantine is commercially available from Merz Pharma GmbH & Co. KgaA. The commercial formulations are used for the treatment of Alzheimer's disease and are sold as NAMENDA in the United States. In Europe, memantine is available under the commercial name AXURA®. Such formulations may readily be used for chronic use in the treatment of OC disorders such as autism.

Alternatively, the memantine may be administered on an "as-needed basis". Preferably the memantine is administered orally or sublingually.

As noted above, suspensions may include oils. Such oil include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Sustained-release preparations may be prepared. Suitable examples of sustained-release preparations include semipermeable matrices of solid hydrophobic polymers containing memantine, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The compositions of the invention may be sterilized by conventional, well known sterilization techniques. The resulting solutions may be packaged for use or filtered under aseptic conditions and lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride and stabilizers (e.g., 1 20% maltose, etc.).

Memantine may also be administered via liposomes, which are small vesicles composed of various types of lipids and/or phospholipids and/or surfactant which are useful for delivery of a drug (such as the antibodies disclosed herein and, optionally, a chemotherapeutic agent). Liposomes include emulsions, foams, micelles, insoluble monolayers, phospholipid dispersions, lamellar layers and the like, and can serve as vehicles to target memantine to a particular tissue as well as to increase the half life of the composition. A variety of methods are available for preparing liposomes, as described in, e.g., U.S. Pat. Nos. 4,837,028 and 5,019,369, which patents are incorporated herein by reference.

Liposomes containing memantine are prepared by methods known in the art, such as described in Epstein et al., Proc. Natl. Acad. Sci. USA 82: 3688 (1985); Hwang et al., Proc. Natl Acad. Sci. USA 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

Example 1

Memantine is Effective at Treating Autism

The present invention is based in part on the surprising discovery that administration of memantine to individuals with symptoms of autism will result in an amelioration of one or more the characteristics of autism. Thus, for the first time, it is shown that autism can be treated using compositions comprising memantine. Such compositions may be administered alone, or in combination with other therapies, including behavior modification regimens. Use of memantine for the treatment of this pervasive developmental disorder is particularly attractive because those of skill in the art are aware of commercial preparations of memantine and safety measures and parameters for preparing useful memantine preparations are also well known to those of skill in the art. The present application describes the first use of memantine in a developmental disorder.

Example summarizes the patient characteristics, comorbid diagnoses and concomitant treatments, memantine dosages and treatment duration, target symptom responses, and side effects of the first six consecutive patients with an autism spectrum disorder treated with memantine. All subjects met DSM-IV TR criteria for an autism spectrum disorder, including autism or pervasive developmental disorder not otherwise specified (PDD-NOS).

As indicated in Table 1, patients ranged in age from 8 years to 13 years of age, and all 6 were male. Four patients met criteria for autism, and 2 for PDD-NOS. Treatment was initiated at 5 mg po qhs for a 2 week duration, and dosage was flexibly titrated up based on treatment response and side effects, by 5 mg every 2 to 4 weeks, to a maximum of 10 mg po BID (20 mg/day). Concomitant medications were generally kept constant for 3 weeks prior to, and during the memantine titration and treatment period. Concomitant medications included atypical antipsychotic agents (i.e., risperidone, aripiperazole, olanzepine), selective serotonin reuptake inhibitors (SSRI's) (ie fluoxetine, fluvoxamine), stimulants (ie methylphenidate) and noradrenergic agents (i.e., clonidine). Comorbid diagnosis included obsessive compulsive disorder (2 patients) and mental retardation (1 patient).

Target symptom improvements noted by expert clinician during careful psychiatric observation included improvement in disruptive behavior (less meltdowns, more mellow, less difficult, less oppositional), social functioning (increased eye contact, more connected, increased listening), cognition and speech/language function (improvement in home tutoring and memory, increased verbal functioning, increased talking). Side effects included slight disinhibition, slight increased mood swings, slight increase in aggression, and slight goofiness.

Table 2 shows further studies monitoring of symptoms in patients being treated using the methods of the present invention.

| Patient | Start Date | Age | Sex | Dx | Dose | Time | Symptoms | Side Effects | Concom Meds | Comorbid Dx |
|---|---|---|---|---|---|---|---|---|---|---|
| 1 AK | 2/11/04 | 10 | M | PDD | 10 mg BID | 13 wks | More mellow Less Meltdown Better behavior Happier 75% improvement in home tutoring, relies on memory not just prompting | Slightly goofy | Risperdal 0.4 mg Fluoxetine 1.2 mg | OCD |
| 2 DS | 2/5/04 | 11 | M | Aut | 5 mg BID | 12 wks | Happy Less Difficult Less oppositional Less disruptive Increased talking | Slight increased mood swings | Aripiprazole 10 mg Fluoxetine 6 mg | OCD |
| 3 DB | 3/12/04 | 13 | M | Aut | 5 mg BID | 9 wks | Increased cognition Increased listening Increased verbal functioning in program Better around house | 10 BID, inc self injury so decr to 5 BID & no side effects | Olazapine 5 mg | MR |
| 4 JS | 3/8/04 | 8 | M | Aut | 10 mg BID | 7 wks | Slight Inc eye contact | Slight Inc self stim Slight dec speech articulation | Risperidal 2.5 mg | — |
| 5 MG | 2/24/04 | 8 | M | Aut | 10 mg BID | 8 wks | Helpful | No SE | Aripiprazole 15 mg Methylphenidate 40 mg | — |
| 6 TM | | 12 | M | PDD | 5 BID | 2 wks | More connected More helpful, but discontinued due to AEs | Disinhibited Aggressive Discontinued-- Secondary to | Fluvoxamine 100 mg Clonadine 0.2 mg | — |

TABLE 2

| Pt | Duration of tx | Age | Sex | Dx | Dose | Symptoms | Side Effects | Concom Meds | Com Dx |
|---|---|---|---|---|---|---|---|---|---|
| 1 | 40 wks | 12 | M | PDD | 5 mg bid | Improved memory, less disruptive IQ gain of 1 SD | Mild disinhibition at 10 mg bid, better on 5 mg bid | Risperdal 0.45 mg Prozac 1.4 mg | OCD PDD |
| 2 | 36 wks | 11 | M | Aut | 5 mg bid | Improved language, reciprocal interactions | Affective lability the first 4 weeks, then decreased | Abilify 15 mg Prozac 6 mg Depakote 1000 mg | Tourette Syndrome |
| 3 | 25 wks | 14 | M | Aut | 5 mg bid | Improved language, attention, behavior Effect tapered off after 20 wks | Self injury at 10 mg bid, better on 5 mg bid | Zyprexa 7.5 mg Abilify 5 mg Trileptal 600 mg | MR |
| 4 | 32 wks | 9 | M | Aut | 5 mg bid | Improved language, reciprocal interactions | Increased stereotypy/tics on 10 mg bid | Risperdal 2.5 mg | Tourette Syndrome |
| 5 | 8 wks | 8 | M | Aut | 10 mg bid | Global improvement | No SE | Abilify 7.5 mg Ritalin 20 mg | — |
| 6 | 2 wks | 12 | M | PDD | 5 mg bid | Improved attention | Disinhibition D/C study | Luvox 100 mg Clonidine 0.2 mg | — |
| 7 | 8 wks | 41 | M | PDD | 5 mg bid | Improved cognition, mood, social reciprocity | Affective lability at 5 mg bid | Lexapro 20 mg Lamictal 250 mg | OCD, BDD |
| 8 | 24 wks | 12 | M | PDD | 5 mg bid | Decreased frustration and meltdowns | | Risperdal 1.0 mg Prozac 30 mg | OCD |
| 9 | 72 wks | 14 | M | Aut | 5 mg bid | Increased eye contact, decreased hitting | Trouble sleeping | Risperdal 2 mg | — |
| 10 | 4 wks | 11 | M | Aut | 5 mg bid | | Slight tremors | Risperdal 0.25 mg | Trisomy 21 History of infantile spasms |
| 11 | 12 | 63 | M | Asp | 10 mg bid | Decreased agitation | Sleeps a lot | Risperdal 1.25 mg Adderall 10 mg Effexor 150 mg | OCPD OCD Narcolepsy |

Example 2

The following Example sets out a protocol for comparing memantine versus placebo in the treatment of autism. Autistic outpatients with IQ>85 are randomized into a 12-week double-blind, placebo-controlled parallel treatment study. Subjects in the treatment and placebo groups are matched for IQ. During the 12 weeks, patients are monitored by the treating physician and assessed by an independent evaluator (IE). The IE will perform study assessments while remaining blind to medication regimens (including possible tapering) as well as any side effects. Study assessments are administered at designated time points.

Procedure

A. Preliminary Phone Screening. Potential subjects are screened using the Seaver Center Screening Questionnaire for Autism to determine suitability for further evaluation.

B. Informed consent. Each patient signs an informed consent document after being informed about the study procedures, risks and potential benefits. A clinical monitor, an independent psychiatrist without a vested interest in the study, evaluates each patient for capacity to provide assent. If the clinical monitor determines a patient (e.g., a child) has the capacity to provide assent, the patient's assent to participate is sought.

C. Diagnostic assessment. Subjects undergo comprehensive evaluation by a study physician who assigned diagnoses based upon the Diagnostic and Statistical Manual of Mental Disorders—Fourth Edition (DSM-IV). Informants of eligible patients are interviewed with the Autism Diagnostic Interview-Revised (ADI-R), and patients are evaluated using the Autism Diagnostic Observation Scale-Generic (ADOSG), to establish an autism diagnosis. These instruments have been demonstrated to be reliable and valid in the assessment and diagnosis of autism. Intellectual functioning is assessed by the WAIS-III. The Vineland Adaptive Behavior Scale is used to assess level of functional ability. Patients who meet diagnostic criteria by both clinical and structured interviews enter the study. Patients with past or present schizophrenia, schizoaffective disorder, organic mental syndromes are excluded from the study.

D. Medical and glutamate gene evaluation. Patients suitable for the study undergo comprehensive medical evaluation by the study psychiatrist or neurologist (medical history, physical examination, routine hematology and blood chemistry, liver profile, urinalysis, pregnancy tests, drug screen). In addition, all patients are tested for the GRIK2 gene haplotype described earlier. Patients with drug screens positive for substances of abuse or positive pregnancy tests are also excluded. Routine hematology, blood chemistry and toxicology is repeated at week 12 or upon termination.

E. Psychotropic medication taper. There are currently no medications approved for the treatment of autism. However, no patients are removed from medications that were providing sufficient benefit to them, as evidenced by a Clinical Global Severity Score of "Y' (Mildly ill) or better. Patients with a Clinical Global Severity Score of "4" (Moderately ill) or greater that are currently taking psychotropic medications underwent a two-week medication-free period before advancing to the randomization stage of the study. The taper is monitored by the study psychiatrist and accomplished in a flexible manner depending on good clinical judgment and patient tolerability.

F. Baseline assessments, informants and randomization. Following the appropriate medication-free period, patients continue to meet with their treating physician, and inclusion and exclusion criteria is reviewed. Patients entering the study undergo the baseline assessments by the study physician and an independent evaluator.

In order to obtain accurate assessments of change for subjects who may need assistance, informants are utilized. The use of an informant is a widely used method for obtaining information regarding intellectually and language impaired individuals (Arnold et al, supra). Informants may be utilized for the following assessments: Vineland, CGI (along with patient when applicable), OAS:M and the Autism Behavior Checklist. The Autism Diagnostic Interview requires an informant. Other assessments are completed through patient observation and interaction. Patients who meet entrance criteria are randomized into their double-blind treatment condition. The pharmacy is provided with the IQ of the subjects before randomization, and the placebo and treatment groups is matched for IQ in three groups: IQ 85-100, 100-115, and >115.

G. 12-week Placebo-Controlled Parallel Treatment. The length of the trial is carefully considered, and a 12-week trial is considered to be fully sufficient for an analysis of safety and efficacy of memantine for autistic adults. A stable therapeutic dose is reached within 4 weeks.

H. Medication and Dosing Schedule. Memantine and placebo is initiated in identical forms of tablets comprising a desired dosage amount. In exemplary embodiments, the dosage is 5 mg/tablet. The tablet may be swallowed whole or crushed. The dose is increased in 5 mg increments to 10 mg twice a day. This dose is maintained for the rest of the trial. Subjects who experience significant side effects and can not tolerate the therapeutic dose are maintained on a lower dose. While the above discussion indicates a dosage of 10 mg to be administered, it should be understood that those of skill in the art may administer more or less depending on the individual being treated. For example, the dosage may comprise 1, 2, 3, 4, 5, 6, 7, 8, 9, 10, 12, 14, 16, 18, 20, or more mg/tablet. Of course multiples of these doses may be administered in any particular administration and it should be understood that the average daily dose may be administered in a single dose or in multiple doses administered during the course of the day.

I. Study Visits. In order to allow for a gradual titration of medication to a therapeutic level and to allow close monitoring of side effects, patients are monitored weekly for the first month of the study. Thereafter, biweekly monitoring takes place. The physician provides advice on the adjustment of the medication as necessary, record side effects and complete the Clinical Global Improvement Scale. The treating physician also offers support in addition to monitoring the clinical state, but without attempts to conduct insight-oriented, cognitive or behavioral therapy. If there is an indication, the study physician meets more regularly than the set schedule to provide closer monitoring of any adverse effects of the medication.

J. Independent Evaluator. As the monitoring of subjects' side effects may prevent the treating psychiatrist from remaining completely blind, an independent evaluator (IE) who is kept blind to side effects is used in this study to conduct study assessments. The ratings performed by the IE is used for the primary analyses. Subjects, informants, and the treating physician are instructed not to disclose side effects and dosing schedule issues to the independent evaluator. As the primary ratings for the study are conducted by a rater who is blind to side effect information (the independent evaluator), it is unnecessary to assess the success of masking the experimental group.

Various publications are cited herein, the contents of which are hereby incorporated by reference in their entireties.

What is claimed is:

1. A method for treating an individual having an autistic disorder comprising administering to said individual a composition comprising memantine or a pharmaceutically acceptable salt thereof in an amount effective to improve a symptom of the disorder, wherein the memantine is administered on an as-needed-basis about one hour before exposure to a stress-inducing situation, wherein the memantine or pharmaceutically acceptable salt thereof is not administered according to a schedule.

2. The method of claim 1, wherein the symptom comprises an impairment in making eye contact with another individual.

3. The method of claim 1, wherein the symptom comprises a lack of social interaction with another individual.

4. The method of claim 1, wherein the symptom comprises a delay in or lack of spoken language.

5. The method of claim 1, wherein the symptom comprises a repetitive pattern of behavior such as arm flapping.

6. The method of claim 1, wherein the symptom comprises hyperactivity.

7. The method of claim 1, wherein the symptom comprises cognitive impairment.

8. The method of claim 1, wherein the symptom comprises attention deficit.

9. The method of claim 1, wherein the as-needed-basis dose of memantine is 0.01 to 500 mg/kg.

10. The method according to claim 1 wherein the composition is administered at least about one hour prior to a point in time at which the improved symptom is desired.

11. The method according to claim 1 wherein the composition is administered in an amount to improve the symptom for at least six hours.

12. The method of claim 1, further comprising administering a serotonin reuptake inhibitor.

13. The method of claim 12, wherein the serotonin reuptake inhibitor is selected from the group consisting of clomipramine, fluoxetine, fluvoxamine, sertraline, paroxetine, citalopram, escitalopram, venlafaxine, mirtazepine, duloxetine and mixtures thereof.

14. The method of claim 1 further comprising administering an anti-epileptic agent.

15. The method of claim 14, wherein said anti-epileptic agent is selected from the group consisting of valproate, divalproex, gabapentin, topiramate, leviracetam, lamotrigine, carbamazapine, oxcarbamazepine, tiagabine, zonisamide, clonzaepam, pregabalin, zarontin and mixtures thereof.

16. The method of claim 1 further comprising administering a stimulant or non-stimulant of attention.

17. The method according to claim 16, wherein said stimulant or non-stimulant of attention is selected from the group consisting of dextroamphetamine, methylphenidate, adderall, adderall XR, concerta, focalin, and strattera.

18. The method of claim 1 further comprising administering an atypical antipsychotic.

19. The method according to claim 18, wherein said atypical antipsychotic is selected from the group consisting of risperidone, olanzepine, quetiapine, ziprasidone, and aripiprazole.

20. The method of claim 1 further comprising administering a cholinergic enhancer.

21. The method according to claim 20 wherein said cholinergic enhancer is selected from the group consisting of aricept (donepezil), excelon, reminyl (galantamine), and mestinon.

* * * * *

UNITED STATES PATENT AND TRADEMARK OFFICE
CERTIFICATE OF CORRECTION

PATENT NO. : 8,461,148 B2  Page 1 of 1
APPLICATION NO. : 11/575483
DATED : June 11, 2013
INVENTOR(S) : Eric Hollander It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 380 days.

Signed and Sealed this
Eighth Day of September, 2015

Michelle K. Lee
*Director of the United States Patent and Trademark Office*